United States Patent [19]
Perry et al.

[11] Patent Number: 5,408,314
[45] Date of Patent: Apr. 18, 1995

[54] DARK CURRENT SUBTRACTION WITH ABBREVIATED REFERENCE CYCLES AND RECURSIVE FILTERING

[76] Inventors: Jeffrey Perry, 10182 Adriana Ave., Cupertino, Calif. 95014; Richard J. Pittaro, 70 Curry Ct., San Carlos, Calif. 94070

[21] Appl. No.: 21,927
[22] Filed: Feb. 24, 1993
[51] Int. Cl.⁶ .............................. G01J 3/44; G01J 3/00
[52] U.S. Cl. ...................................... 356/301; 356/300; 356/319
[58] Field of Search ............... 356/300, 301, 319, 325, 356/398

[56] References Cited
U.S. PATENT DOCUMENTS

| | | | |
|---|---|---|---|
| 4,193,690 | 3/1980 | Levenson et al. | 356/301 |
| 4,397,556 | 8/1983 | Müller | 356/301 |
| 4,407,008 | 9/1983 | Schmidt et al. | 356/301 |
| 4,586,819 | 5/1986 | Tochigi et al. | 356/301 |
| 4,648,714 | 3/1987 | Benner et al. | 356/301 |
| 4,678,277 | 7/1987 | Delhaye et al. | 356/301 |
| 4,784,486 | 11/1988 | Van Wagenen et al. | 356/301 |
| 4,953,976 | 9/1990 | Adler-Golden et al. | 356/301 |
| 4,984,085 | 1/1991 | Landowski | 358/213 |
| 5,132,801 | 7/1992 | Yamano | 358/213 |

Primary Examiner—Rolf Hille
Assistant Examiner—David Ostrowski

[57] ABSTRACT

A method and apparatus for performing dark signal correction on a photoelectric conversion device. A flow of light to the device is alternately conducted and interrupted. The device generates an intermixed signal while the flow of light is conducted to the device, the intermixed signal including a desired signal intermixed with an unwanted dark signal. The device generates a dark signal alone while the flow of light to the device is interrupted. The dark signal alone is filtered to produce a filtered dark signal. The filtered dark signal is subtracted from the intermixed signal to produce a corrected signal, which is representative of the desired signal.

14 Claims, 7 Drawing Sheets

DARK CURRENT SUBTRACTION WITH ABBREVIATED REFERENCE CYCLES AND RECURSIVE FILTERING

BACKGROUND

The present invention is generally directed to a method and apparatus for dark signal correction, and more particularly to a method and apparatus for correcting an unwanted dark signal of a photoelectric conversion device employed in spectrographic analysis of gaseous substances.

Instrumentation that analyzes gaseous substances is required in a variety of important applications. For example, during a surgical operation, patients are anesthetized through the careful administration of gases. The supply of these anesthetics must be regulated with great precision. In addition, the gases expelled in the patient's breath need to be monitored continuously to determine the condition of the patient. Instrumentation that analyzes gases exhaled by patients provide vital information to surgical personnel.

A particular class of instrumentation employs Raman spectroscopy to detect the presence and concentration of gaseous substances. Scattering of light by the Raman effect has received much attention from scientists since its original exposition by C. V. Raman in 1928. Instrumentation that employs the Raman effect provides a light, such as a laser beam, which illuminates molecules of a gas disposed within a sampling cell. Molecular vibrations of the gas cause the light to scatter off the illuminated gas molecules to produce scattered light in a process which shifts the frequency of the scattered light by exactly the vibrational frequency of the molecule. The frequency shift of the spectral signal is characteristic of the gas being analyzed and is independent of the frequency of the illuminating light. Thus, the Raman scattered light can be used to infer properties of the gas being analyzed, such as chemical composition and concentration.

The Raman scattered light is collected from the gas disposed within the sampling cell and constituent frequency components of the light are analyzed and detected. The analyzed frequency components are used to produce a spectrogram, which can be displayed on a display device. By interpreting the spectrogram, the presence and concentration of different types of constituent gas molecules in the gas can be deduced. Though the Raman effect can be employed to provide a powerful analytical tool, it should be noted that in general, intensity of the light produced by the Raman effect is extremely weak. The Raman scattered light has an extremely low intensity relative to intensity of radiation used to stimulate the effect.

Instrumentation that employs the Raman effect is described in U.S. Pat. No. 4,648,714 entitled "Molecular Gas Analysis By Raman Scattering in Intracavity Laser Configuration" by Benner et al. issued Mar. 10, 1987, and in U.S. Pat. No. 4,784,486 entitled "Multichannel Molecular Gas Analysis By Laser-Activated Raman Light Scattering" by Van Wagenen et al. Because each of these patents provides helpful background information, they are incorporated herein by reference. The instrumentation described in each of these two patents provides a laser beam that illuminates molecules of a gas disposed within a sampling cell. Raman scattered light generated by the Raman-effect is collected from the gas disposed within the sampling cell.

Each patent includes discussions focussing on a respective means for detecting constituent frequency components of the Raman scattered light. Van Wagenon et al. teach that a photomultiplier tube is used to detect the Raman scattered light. Benner et al. teach that any suitable state of the art detector such as a photo diode, intensified diode array or photomultiplier tube may be used.

Though photoelectric conversion devices such as photo diodes, photomultipliers or the like can be employed as discussed by Van Wagehen and Benner to detect Raman scattered light, certain difficulties still remain. A practical limitation of such photoelectric conversion devices is that if the devices are exposed to Raman scattered light, then the devices produce electrical signals that include a desired signal intermixed with an unwanted dark current signal. The desired signal is generated in response to the Raman scattered light. The unwanted dark current signal is generated independently of any illumination of the photoelectric conversion device. If the photoelectric conversion device is shielded from exposure to light, a dark signal alone is directly measurable at an output of the device. Thus it is easy to analyze the dark signal alone without producing the desired signal. Unfortunately, there is no way known for the photoelectric conversion device to directly produce the desired signal without also producing the dark signal intermixed therewith. It is difficult to isolate the desired signal because the desired signal is inherently intermixed with the unwanted dark signal.

Problems arise because the dark signal tends to obscure the desired signal. Such a negative effect of the dark signal is especially prominent in Raman spectroscopy wherein the photoelectric conversion device is employed to detect the Raman scattered light. Because the intensity of light produced by the Raman effect is extremely weak, the desired signal produced by the photoelectric conversion device in response to the Raman scattered light is a weak signal. Because the desired signal is so weak, the desired signal is especially susceptible to being obscured by the dark signal intermixed therewith.

Some correction schemes provide a partial solution to the problems caused by the dark current signal. A fixed correction scheme employs a fixed compensating signal in an attempt to correct the electrical signal produced by the photoelectric conversion device exposed to Raman scatted light. The fixed compensating signal is subtracted from the electric signal to produce a corrected signal. The fixed compensation scheme has some effectiveness at removing fixed signal artifacts of the dark signal contributed by charge injection of multiplexers, reset circuits and op-amps commonly used in conjunction with photodiodes and diode arrays. However, taken as a whole, the fixed correction scheme has only limited success because the dark signal also includes variable signal artifacts. For example, experiments show that the dark signal is a strong function of temperature of the photoelectric conversion device. Therefore, it is theorized that the dark signal includes a variable thermal artifact. For most semiconductor photoelectric conversion devices, the dark signal approximately doubles for every 7 degrees Celsius increase in temperature of the photoelectric conversion device. Because the fixed compensating signal does not adapt to variable signal artifacts of the dark signal, a better correction scheme is needed.

A variable correction scheme employs a pair of similarly constructed photoelectric conversion devices that are thermally coupled so as to be in thermal equilibrium with one another. A first member of the pair of conversion devices is exposed to Raman scattered light in a similar manner as discussed previously, thereby producing a first electric signal that includes a desired signal intermixed with a first dark signal. A second dark signal is generated by shielding a second member of the pair of photoelectric conversion devices from exposure to light. Because the first and second devices are similarly constructed, it is theorized that the first dark signal is similar to the second dark signal. Furthermore, since the pair of devices are in thermal equilibrium with one another, it is theorized that thermal variations in the first dark signal are tracked by the second dark signal. The variable compensation scheme is intended to compensate for the effect of the first dark signal upon the desired signal by subtracting the second dark signal from the first electric signal to produce a corrected signal that is thermally adjusted.

Unfortunately, the variable correction scheme adds noise to the corrected signal produced thereby. Each dark signal produced includes a respective noise artifact. For example, a first noise artifact is present in the first dark signal, and a second noise artifact is present in the second dark signal. Therefore, in addition to inheriting the first noise artifact from the first dark signal, the corrected signal produced by the variable correction scheme also inherits the second noise artifact from the second dark signal. Accordingly, the corrected signal produced by the variable correction scheme includes approximately twice the noise of the corrected signal produced by the fixed correction scheme discussed previously. A further problem with the variable correction scheme is that it is inherently inefficient since a pair of conversion devices are required while only one member of the pair directly contributes to generating the desired signal.

While the fixed correction scheme and the variable correction scheme each make contributions, they also each have limitations. Because the desired signal produced in Raman spectroscopy is extremely weak, any corrected signal derived therefrom is especially susceptible to being obscured by additional noise. Therefore an efficient dark signal correction method and apparatus are needed to compensate for fixed and variable signal artifacts of the dark signal, while reducing noise added by the correction method and apparatus. Furthermore, the dark signal correction method and apparatus should remain efficient while regularly monitoring and correcting the intermixed signal, so that a corrected signal produced thereby can be advantageously used to provide a corrected real-time display to a doctor monitoring a patient undergoing anesthesia.

SUMMARY OF THE INVENTION

The present invention provides an efficient method and apparatus for performing dark signal correction of a desired signal produced by a photoelectric conversion device while substantially preserving fidelity of the desired signal. Briefly and in general terms the present invention provides a flow of light to a photoelectric conversion device. The flow of light to the device is alternately conducted and interrupted. While the flow of light is conducted to the device, the device produces an intermixed signal, which includes the desired signal intermixed with an unwanted dark signal. The desired signal is generated by the device in response to the flow of light. While the flow of light to the device is interrupted, the device generates a dark signal alone. The dark signal alone is filtered to reduce noise artifacts present therein. The filtered dark signal is then subtracted from the intermixed signal to produce a corrected signal representative of the desired signal. Because the corrected signal represents the desired signal at a preferred level of sensitivity and accuracy, the corrected signal produced by the present invention preserves the fidelity of desired signal.

The efficiency, sensitivity and accuracy of the preset invention make important contributions to spectrographic analysis. These contributions are especially valuable in Raman spectroscopy of a surgical patient's air way gasses, wherein light produced by the Raman effect is already extremely weak. Accordingly, the present invention is particularly well adapted to Raman spectroscopy of gasses. For example, a sample material, such as a gas, is stimulated to generate a flow of light therefrom by the Raman effect. The flow of light is spectrally separated by a frequency separation means, such as a diffraction grating, and directed to the photoelectric conversion device. The flow of light from the sample material to the device is alternately conducted and interrupted. The photoelectric conversion device generates the intermixed signal which includes the desired signal intermixed with the dark signal as described previously herein. During interruption of the flow of light, the conversion device generates the dark signal alone, which is then filtered to produce the filtered dark signal. The filtered dark signal is subtracted from the intermixed signal to produce the corrected signal. A spectrogram is then generated from the corrected signal.

The present invention provides a novel method and apparatus for performing dark signal correction. Other aspects and advantages of the present invention will become apparent from the following detailed description, taken in conjunction with the accompanying drawings, illustrating by way of example the principles of the invention.

DETAILED DESCRIPTION OF PREFERRED EMBODIMENT

Figure 1:
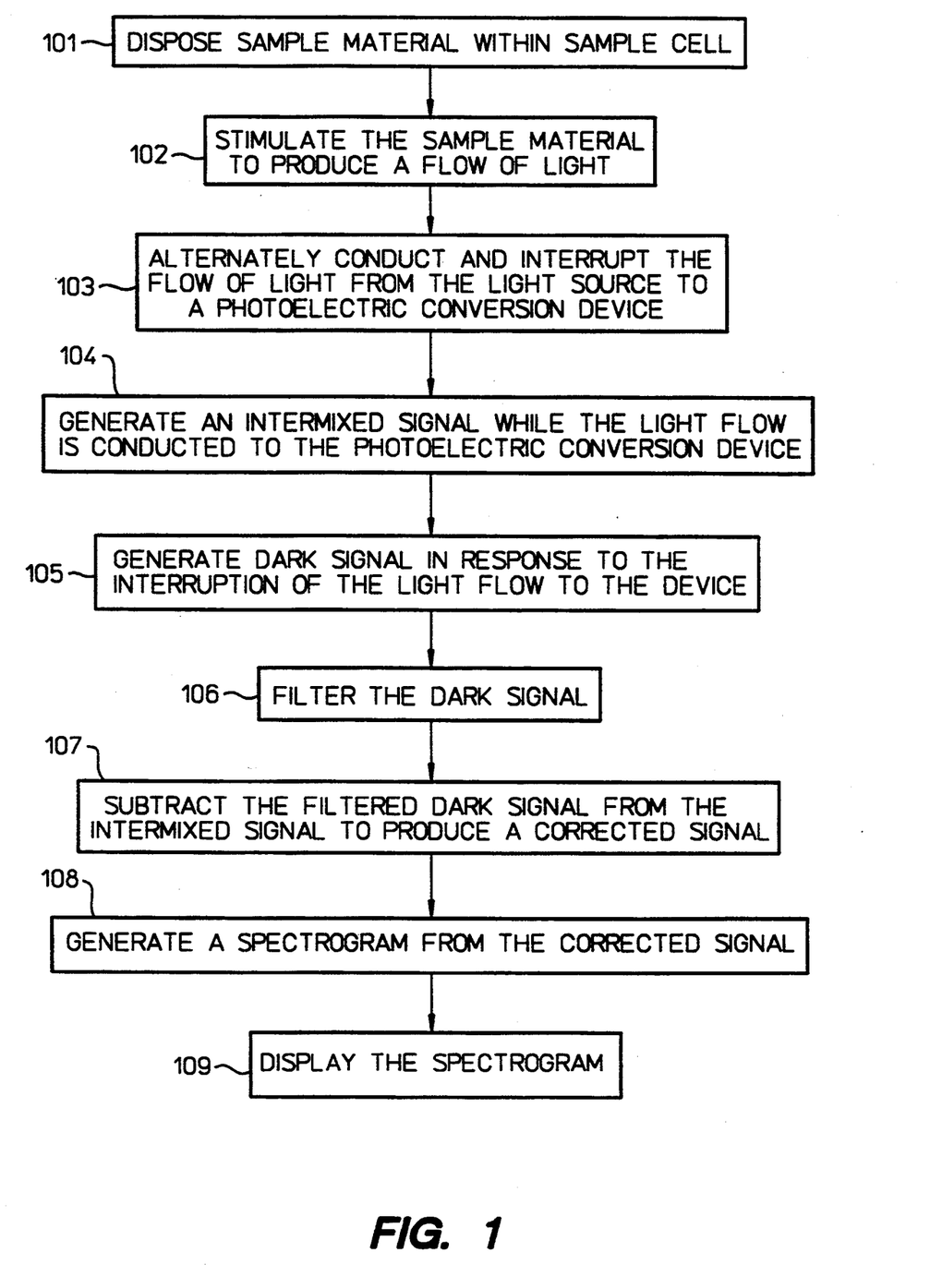
FIG. 1 is a flow chart illustrating a preferred embodiment of the method of the present invention.
Figure 2:
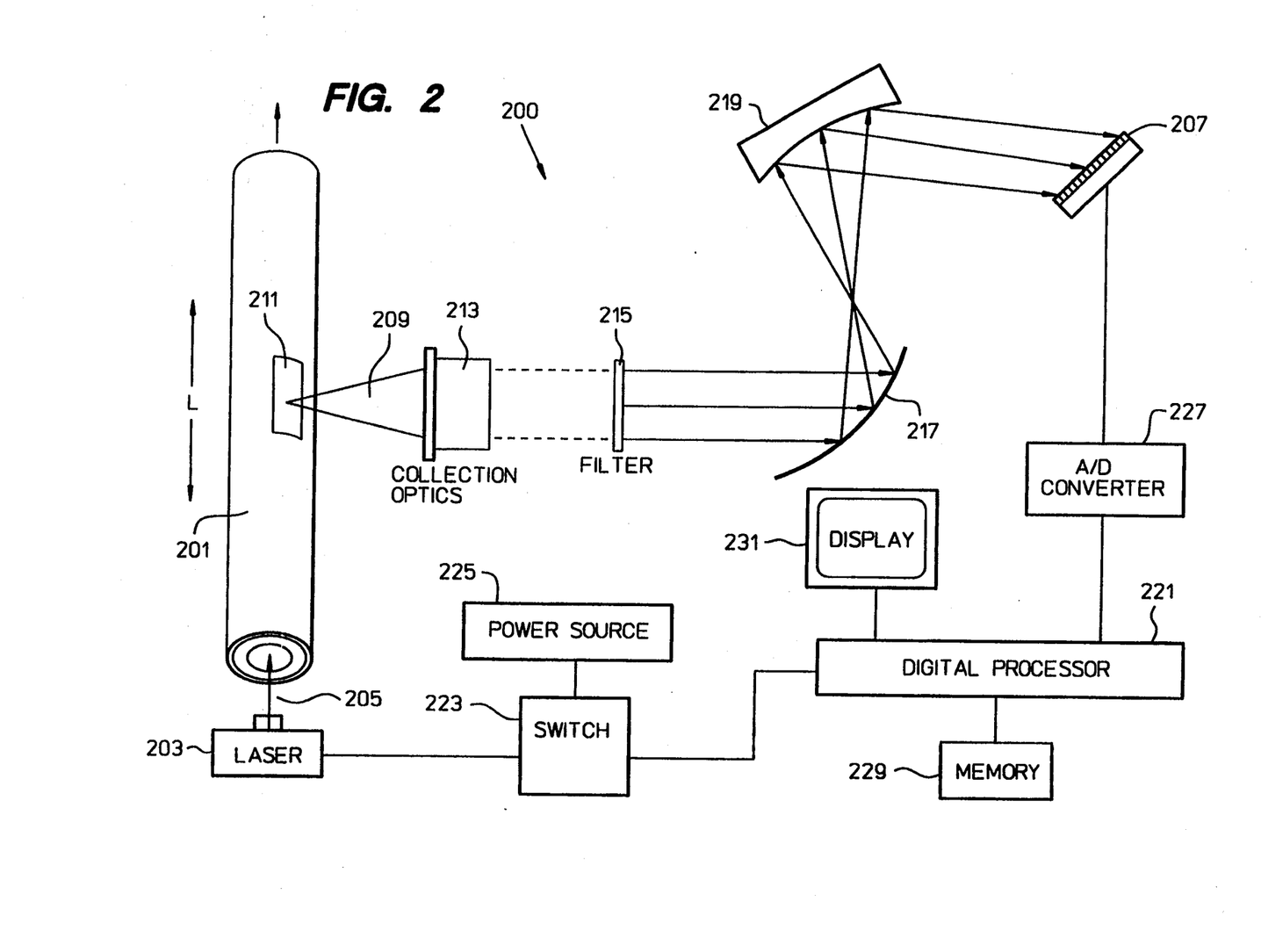
FIG. 2 is a partial block diagram of a preferred spectrographic analysis system used in conjunction with a preferred embodiment of the present invention.

A preferred embodiment of a dark signal correction method of the present invention is illustrated in a flow chart shown in FIG. 1. As indicated by block 101 of the flow chart, a sample material to be analyzed is disposed within a sample cell of a spectrographic analysis system. The principles of the invention will be further illustrated using a partial block diagram as shown in FIG. 2 illustrating a preferred spectrographic analysis system 200 used in conjunction with the preferred embodiment of the present invention. During normal operation of the system, the sample material to be analyzed is disposed within a sample cell. For example, in order to analyze a flow of breath from a surgical patient, the flow of breath is disposed within the sample cell. Exemplary constituent gasses of interest in the breath of the surgical patient include common gasses, such as oxygen ($O_2$) and carbon dioxide ($CO_2$), as well as one or more anesthetic gasses such as halothane ($CF_3$—$CHClBr$) and isoflurane ($CF_3$—$CHCl$—$O$—$CHF_2$). In the preferred embodiment, the sample cell comprises a hollow tube wherein the flow of breath is pumped through the hollow tube for analysis. For example, FIG. 2 shows a preferred sample cell 201 comprising a hollow glass tube having a reflective outer surface coating.

As indicated by block 102 of the flow chart of FIG. 1, the sample material is stimulated to produce a flow of light 209 therefrom by Raman scattering. An intense radiation beam, such as that produced by laser action, is used to stimulate the sample material disposed within the sample cell. As shown in the block diagram of FIG. 2, a laser 203 is optically coupled to the reflective tube of the sample cell. If the laser is deactivated, then no light is produced. If the laser is activated, then the laser produces a laser beam 205 that projects through the hollow tube, along a longitudinal axis, L, of the hollow tube. The laser beam interacts with the sample material disposed within the tube, stimulating the sample material. While the laser beam stimulates the sample material, the stimulated sample material is a light source that produces a flow of light therefrom by Raman scattering. As will be explained in greater detail later herein, the present invention provides a means for alternately conducting and interrupting the flow of light from the light source to a photoelectric conversion device 207, shown in FIG. 2. Since the flow of light produced by the Raman effect depends upon the laser beam stimulating the sample material, in the preferred embodiment the flow of light from the light source to the photoelectric conversion device is alternately conducted and interrupted by means of alternately activating and deactivating the laser.

In the preferred embodiment, the laser beam shown in FIG. 2 illuminates constituent gas molecules of the surgical patient's breath disposed within the sampling cell, stimulating the Raman effect. Accordingly, molecular vibrations of the gas cause the light to scatter off the illuminated gas molecules, thereby producing the flow of Raman scattered light in a process that shifts the frequency of the scattered light by exactly the respective vibrational frequency of each molecule. The frequency shift of the scattered light produces spectral lines characteristic of the gas being analyzed and is independent of the frequency of the illuminating light. Thus properties of the gas being analyzed, such as chemical composition and concentration, can be inferred from examination of the flow of Raman scattered light. Though the Raman effect provides a powerful analytical tool, it should be noted that in general the light produced by the Raman effect is extremely weak. The Raman scattered light has an extremely low intensity relative to intensity of radiation used to stimulate the effect.

The reflective coating of the tube helps to concentrate the flow of Raman scattered light and substantially contains much of the Raman scattered light within the tube by reflection. As shown in FIG. 2, the flow of Raman scattered light 209 is allowed to pass from the tube through a glass wall of the tube and through an aperture 211 in the reflective coating of the tube. It should be understood that while it is preferred that the sample cell comprises a hollow reflective tube as described herein, the present invention may also be practiced with beneficial results for a sample cell formed by some other structure.

As shown in FIG. 2, collection optics 213 positioned adjacent to the aperture collect the flow of Raman scattered light therefrom. A laser line rejection filter 215 is optically coupled to the collection optics to block any scattered light at the wavelength of the laser beam. An optical assembly 217 optically coupled to the filter directs the flow of light to a frequency separation means, such as a concave diffraction grating 219, as shown in FIG. 2. The diffraction grating separates frequency components of the flow of light, dispersing spectral lines characterizing the sample material across an array of sensor elements of the photoelectric conversion device 207.

The photoelectric conversion device is optically coupled to the frequency separation means for receiving the flow of light therefrom. The photoelectric conversion device is preferably a silicon photodiode array of approximately 256 sensor elements, but can be a larger or smaller array of PIN photodiodes (each respectively comprising a sandwich of P type, Intrinsic, and N type semiconductors) or a CCD array (Charge Coupled Devices). Each sensor element of the array corresponds to at least one spectral line of the constituent frequency components of the flow of Raman scattered light. Thus, the array of photosensor elements simultaneously receives an entire spectrum of light scattered from the sample material by the Raman effect.

As indicated in block 103 of the flow chart of FIG. 1, in accordance with the method of the present invention the flow of light from the light source to the photoelectric conversion device is alternately conducted and interrupted. As indicated previously, since the flow of light produced by the Raman effect depends upon the laser beam stimulating the sample material, in the preferred embodiment the flow of light from the light source to the photoelectric conversion device is alternately conducted and interrupted by alternately activating and deactivating the laser. As shown in the block diagram of FIG. 2, in the preferred embodiment a digital processor 221 controls operation of the laser. The digital processor, essentially embodied in a microprocessor, is electrically coupled to a switch 223. The switch is coupled to a power source 225 and the laser 203 for switching power from the power source to the laser. The digital processor activates the laser by controlling the switch to conduct a flow of power from the power source to the laser, thereby energizing the laser to produce the laser beam. The digital processor deactivates the laser by controlling the switch to interrupt the flow of power from the power source to the laser, thereby preventing the laser from producing light.

It should be understood that alternative means for alternately conducting and interrupting the flow of light are employed with beneficial results. For example, in a first alternative embodiment the digital processor is not coupled to the power switch to activate and deactivate the laser. Instead, the digital processor is coupled to an electro-mechanical shutter, which is positioned between the laser and an entrance to the hollow tube. If the shutter is activated by the digital processor, then the shutter opens, allowing the laser beam to enter the tube and stimulate the sample material disposed therein. If the shutter is deactivated by the digital processor, then the shutter closes to block the laser beam from entering the tube and stimulating the sample material disposed therein. Since the flow of light produced by the Raman effect depends upon the laser beam stimulating the sample material, in the first alternative embodiment the shutter is alternately activated and deactivated so that the flow of light from the light source to the photoelectric conversion device is alternately conducted and interrupted.

In a second alternative embodiment, the shutter is positioned between the collection optics and the aperture in the reflective coating of the tube, instead of being positioned between the laser and the entrance to the tube as in the first alternative embodiment. If the shutter is activated by the digital processor, then the shutter opens, allowing the flow of concentrated Raman scattered light to be collected by the collection optics. If the shutter is deactivated by the digital processor, then the shutter closes to block the flow of Raman scattered light from being collected by the collection optics.

Regardless of whether the power switch of the preferred embodiment is employed or the mechanical shutter of the alternative embodiments is employed, a similar result of alternately conducting and interrupting the flow of light to the photoelectric conversion device is achieved. Accordingly, it should be clear that the present invention should not be construed as being unduly limited to only one particular embodiment of the means for alternately conducting and interrupting the flow of light to the photoelectric conversion device.

By alternately conducting and interrupting the flow of light to the photoelectric conversion device, the present invention efficiently generates needed signals. While the flow of light is conducted to the photoelectric conversion device, the photoelectric conversion device generates an intermixed signal comprising a desired signal intermixed with an unwanted dark signal, consistent with block 104 of the flow chart of FIG. 1. However while the flow of light to the photoelectric conversion device is interrupted, the photoelectric conversion device generates a dark signal alone, consistent with block 105 of the flow chart of FIG. 1.

The present invention provides a means for processing the dark signal alone to filter out unwanted noise artifacts therefrom, thereby producing a filtered dark signal consistent with block 106 of the flow chart of FIG. 1. As will be discussed in greater detail later herein, in the preferred embodiment digital filtering techniques are used to produce the filtered dark signal. As shown in the block diagram of FIG. 2, an analog to digital converter 227 is electrically coupled to the photoelectric conversion device for generating a set of dark signal values based upon the dark signal alone. As shown in the block diagram of FIG. 2, the digital processor is electrically coupled to the analog to digital converter and to a memory device 229, which stores program instructions and intermediate data values for digitally filtering the dark signal values. It should be understood that although digital filtering techniques are preferred, the present invention is not strictly limited to digital methods, since analog methods of filtering are alternatively employed with beneficial results. For example in alternative embodiments, active analog filters process the dark signal alone to filter out unwanted noise artifacts therefrom. Such active analog filters are constructed using operational amplifiers suitably coupled to networks of reactive elements such as inductors and capacitors.

Consistent with block 107 of the flow chart, the present invention further provides a means for subtracting the filtered dark signal from the intermixed signal to produce a corrected signal, which is representative of the desired signal. It is preferred that such subtraction be performed digitally, for example the analog to digital converter shown in FIG. 2 digitizes the intermixed signal. The digital processor is coupled thereto for receiving the digitized intermixed signal. The distal processor is suitably programmed to subtract the filtered dark signal values from the digitized intermixed signal to produce a corrected signal value. It should be understood that although digital techniques are preferred, the present invention is not strictly limited to such digital techniques, since analog methods of subtraction are alternatively employed. In alternative embodiments, analog subtraction is performed, for example, by using a differential amplifier.

Consistent with block 108 of the flow chart of FIG. 1, the processor generates a spectrogram from the corrected signal. As shown in the block diagram of FIG. 2, a display device is coupled to the digital processor. Consistent with block 109 of the flow chart of FIG. 1, the digital processor is programmed to display the spectrogram on the display device.

Figure 3A:
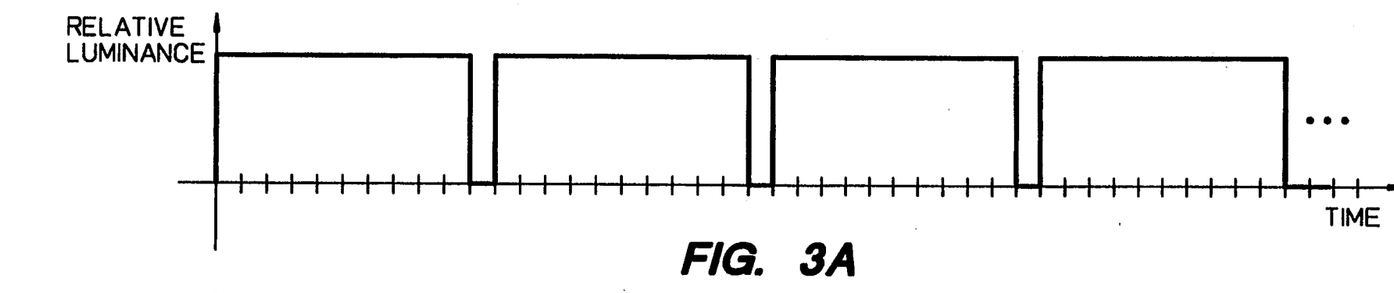
FIG. 3A is a timing diagram representing a flow of light that is alternately conducted and interrupted during regular time durations in accordance with the preferred embodiment of the present invention.

In the preferred embodiment, the step of alternately conducting and interrupting the flow of light, as discussed previously with respect to block 103 of the flow chart of FIG. 1, includes interrupting the flow of light during regular time durations so that the dark signal generated by the photoelectric conversion device comprises regular dark signal samples. FIG. 3A shows a timing diagram representing the flow of light that is alternately conducted and interrupted during regular time durations. It is preferred that the digital processor controls the flow of light to the photoelectric conversion device so that time periods of light conduction are much longer than time periods of light interruption, thereby augmenting an amount of light available to the device for generating the intermixed signal. For example, as shown in FIG. 3A, each time period of light conduction is ten times longer than each time period of light interruption. Since Raman scattered light is extremely weak as discussed previously, it is especially desirable to augment any Raman scattered light available to the device for generating the intermixed signal.

Figure 3B:
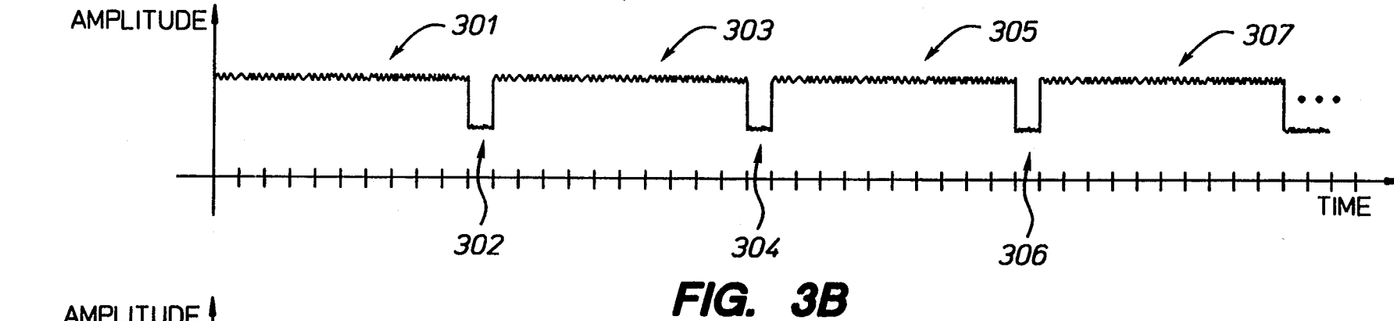
FIG. 3B is a timing diagram representing signals produced by a photoelectric conversion device optically coupled to the flow of light represented in FIG. 3A.
Figure 3C:
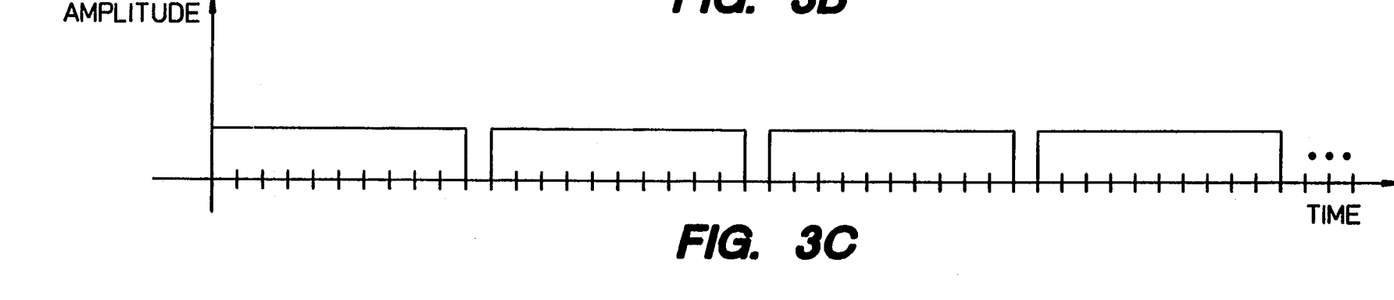
FIG. 3C is a timing diagram illustrating a corrected signal produced by the present invention.

FIG. 3B shows a timing diagram representing electrical signals produced by the photoelectric conversion device. Comparing FIG. 3A to 3B, it is apparent that while the flow of light is conducted to the photoelectric conversion device, as illustrated by plateaus in the timing diagram of FIG. 3A, the photoelectric conversion device generates the intermixed signal. The intermixed signal comprises intermixed signal samples 301, 303, 305, 307 as shown by plateaus in the timing diagram of FIG. 3B. As discussed previously, while the flow of light is interrupted, the photoelectric conversion device generates the dark signal alone. In the preferred embodiment, the flow of light to the photoelectric conversion device is interrupted during regular time durations as illustrated by steep wells having regular time durations in the timing diagram of FIG. 3A, so that the dark current signal alone comprises dark signal samples 302, 304, 306, as illustrated by steep wells in the timing diagram of FIG. 3B. The dark signal samples are filtered and suitably subtracted from the intermixed signal to produce the corrected signal, which is representative of the desired signal. For example, if each time period of light conduction is ten times longer than each time period of light interruption as illustrated in FIG. 3A, then the filtered dark signal samples are scaled up by a factor of ten and subtracted from the intermixed signal to produce the corrected signal. FIG. 3C is a timing diagram to illustrate the corrected signal. Preferably, the dark signal samples are digitized by the analog to digital converter to produce a set of dark signal sample values, which are then digitally filtered, scaled, and subtracted from the intermixed signal. In the preferred embodiment, the regularity of the dark signal samples is employed by the present invention to advantageously provide a corrected real-time display to a doctor monitoring a patient undergoing anesthesia.

Figure 4A:
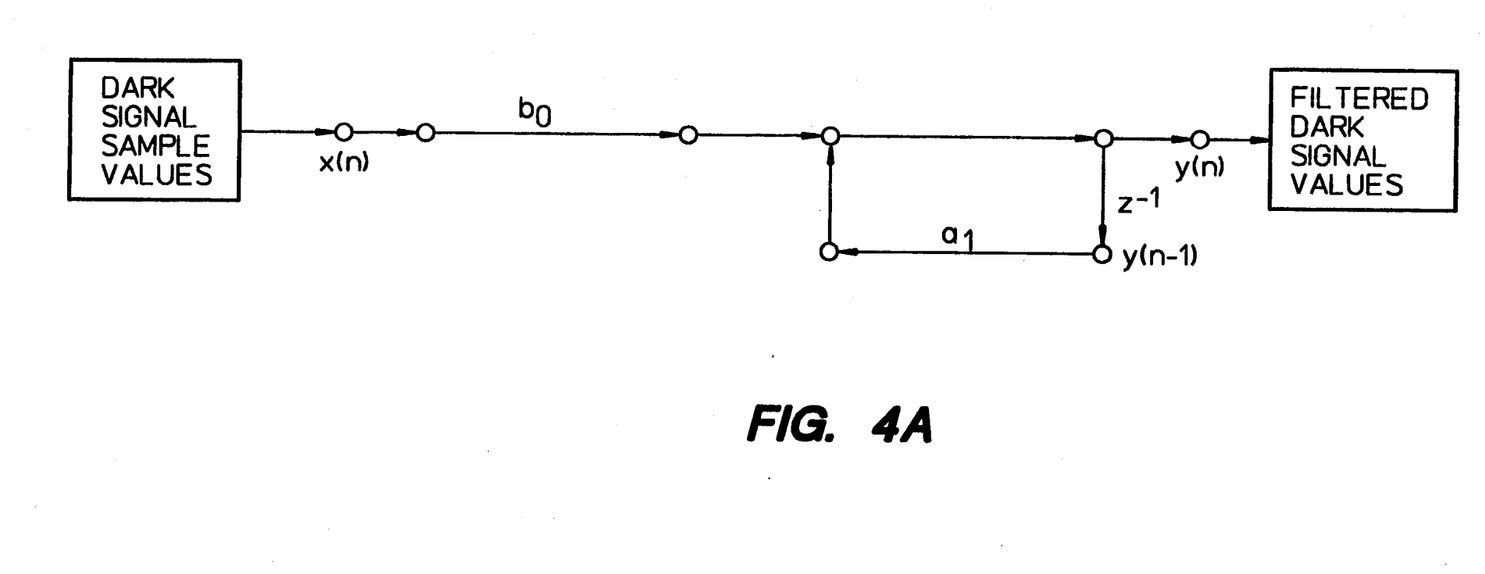
FIG. 4A is a data flow diagram representing a single pole infinite impulse response digital filter for filtering regular dark signal samples in accordance with the preferred embodiment of the present invention.

In the preferred embodiment, the digital processor of the present invention is programmed to digitally factor the dark signal sample values in accordance with a single pole Infinite Impulse Response (IIR) digital filter method. The filtering method is a recursive method described by a difference equation, referred to herein as Eq. 1:

$$y(n) = a_1 y(n-1) + b_0 x(n)$$

where y(n) is an nth member of a set of recursively filtered dark signal values, y(n-1) is a previous, n-1th member of the set of recursively filtered dark signal values, x(n) is an nth member of the set of dark signal sample values. Coefficients $a_1$ and $b_0$ are chosen using known techniques in order to provide sufficient rejection of undesired frequency components of the dark signal, depending on spectral characteristics of the dark signal. FIG. 4A is a signal flow graph of the single pole IIR digital filter method consistent with Eq. (1). In the preferred embodiment the set of dark signal sample values are derived from a large set of the regular dark signal samples. For example a large set having membership on the order of 100 samples produces beneficial results. It is preferred that the filter be a sliding filter that continually adapts itself to filter recent dark signal sample values. For example, given a total sample width of 100 samples, the filter "slides" to filter the most recent 100 dark signal samples, thereby consistently providing a recent set of filtered dark signal values.

Figure 4B:
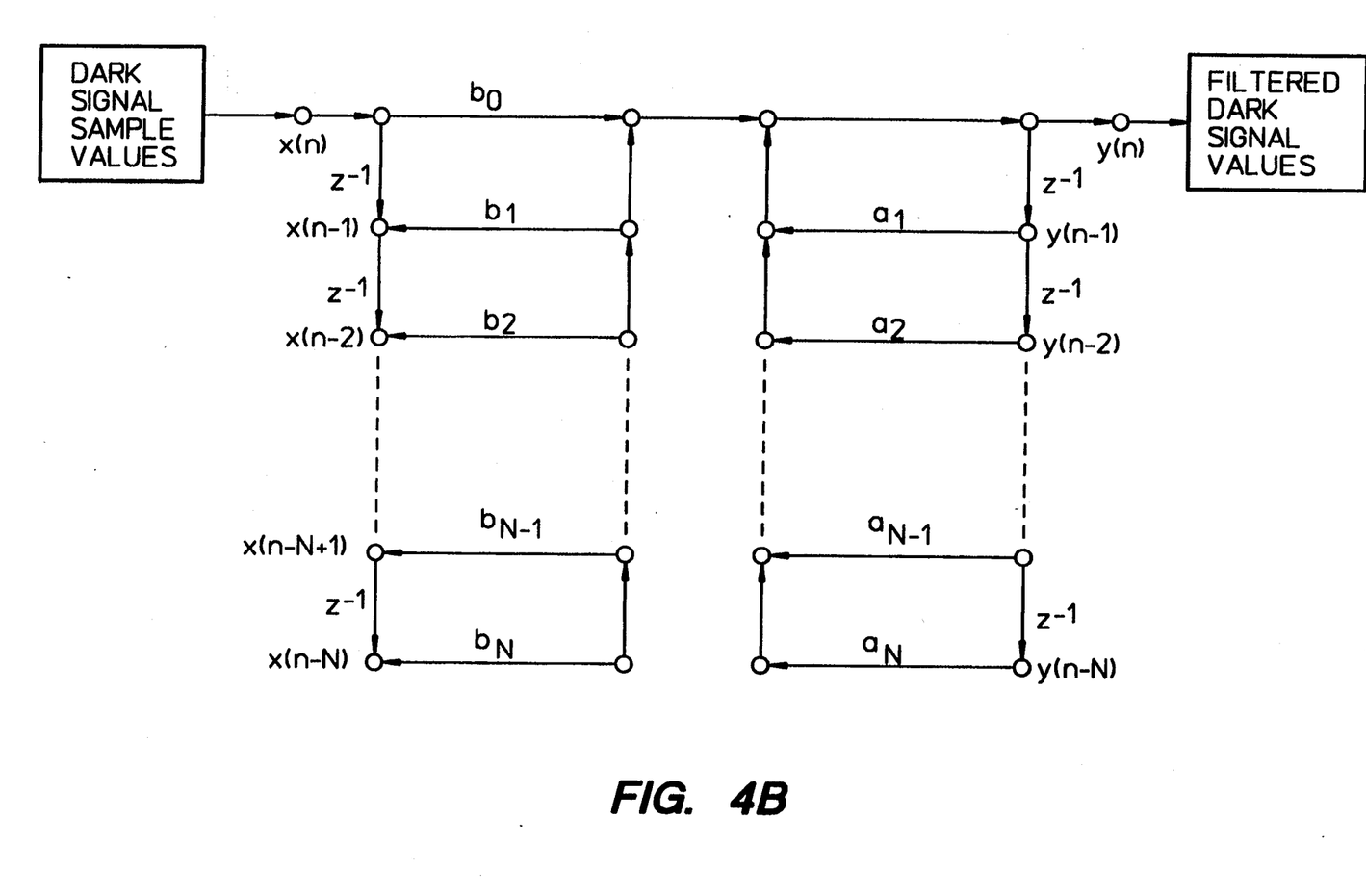
FIG. 4B is a generalized version of the data flow diagram of FIG. 4A, representing an N pole infinite impulse response digital filter.

It should be understood that while more sophisticated digital filtering methods are employed with beneficial results, such methods generally take longer to compute results. Therefore there is often some trade-off between greater filtering performance of the more sophisticated methods and the capacity of the invention to advantageously provide the corrected real-time display to the doctor, as discussed previously. A recursive filtering method is broadly described herein as employing an IIR digital filter having multiple poles and zeroes, consistent with another difference equation, referred to herein as Eq. 2:

$$y(n) = \sum_{k=1}^{N} a_k y(n-k) + \sum_{k=0}^{M} b_k x(n-k)$$

where y(n) is an nth member of a set of recursively filtered dark signal values, y(n-k) is a previous, n-kth member of the set of recursively filtered dark signal values, x(n-k) is an n-kth member of the set of dark signal sample values, and $a_k$ and $b_k$ represent suitably chosen constants. FIG. 4B is a signal flow graph consistent with the digital filtering method described in Eq. (2). A benefit of employing recursive digital filtering techniques is that they make particularly efficient use of memory resources.

Figure 5:
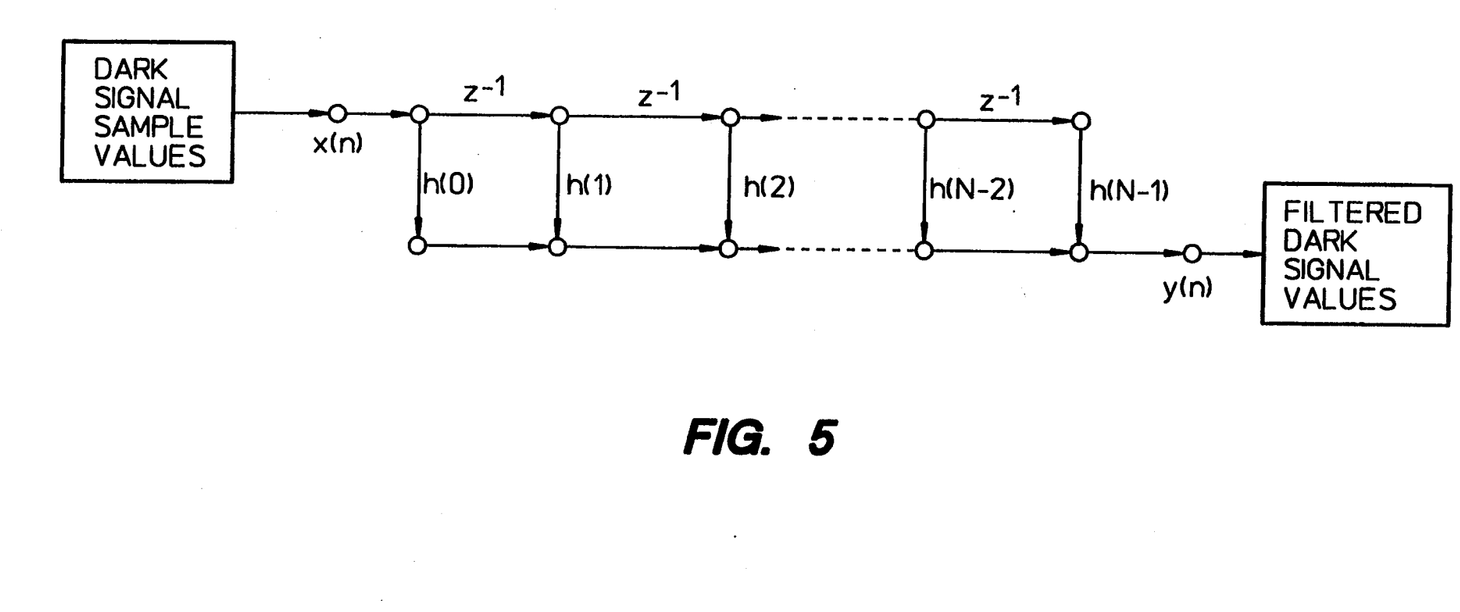
FIG. 5 is a data flow diagram representing an N pole finite impulse response digital filter for filtering regular dark signal samples in accordance with alternative embodiments of the present invention.

In an alternative embodiment, the digital processor of the present invention is programmed to digitally filter the dark signal sample values in accordance with a Finite Impulse Response (FIR) digital filter method. The filtering method is a non-recursive method described by a difference equation, referred to herein as Eq. 3:

$$y(n) = \sum_{k=0}^{N-1} h(k) x(n-k)$$

where y(n) is an nth member of a set of recursively filtered dark signal values, x(n-k) is an n-kth member of the set of dark signal sample values, and h(k) represents suitably chosen constants. FIG. 5A is a signal flow graph consistent with the digital filtering method described in Eq. (3). Digital filtering methods are discussed in detail in chapters 4 and 5 of "Digital Signal Processing" by Alan V. Oppenheim and Ronald W. Shafer, Prentice Hall 1975, pp. 136-283. Because these chapters provide helpful supportive teachings, they are incorporated herein by reference.

Furthermore, a fixed compensation method may also be employed in conjunction with the digital filtering method. In the fixed compensation method, the digital processor subtracts a fixed compensating value from the dark signal samples that are filtered. The fixed compensation method removes fixed signal artifacts of the dark signal contributed by charge injection of multiplexers, reset circuits and op-amps commonly used in conjunction with photodiodes and diode arrays. Since the fixed signal artifacts are time invariant, the fixed compensating value may be initially computed by the processor at system start up and then used continuously during system operation.

Figure 6A:
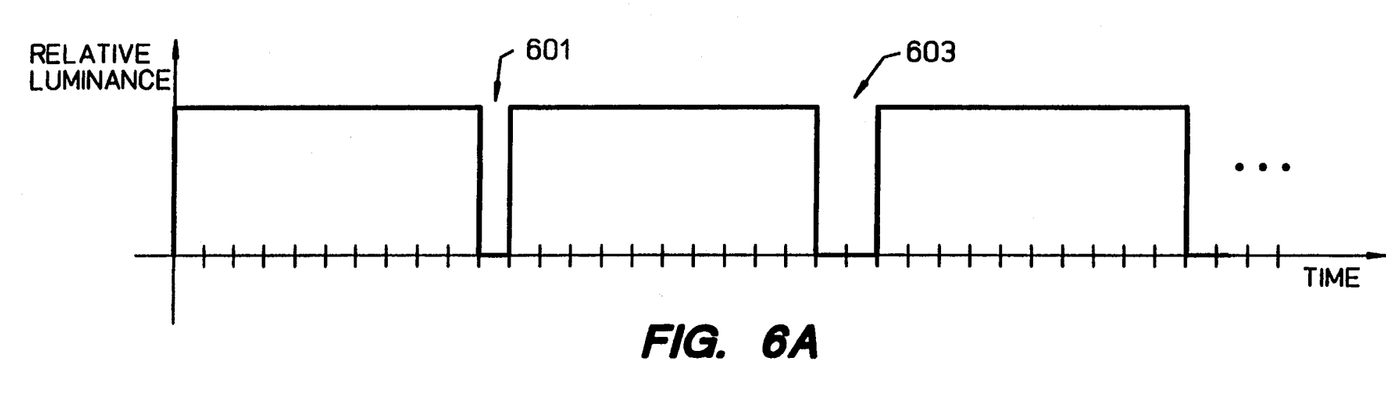
FIG. 6A is a timing diagram representing light flow interruption during system start up.
Figure 6B:
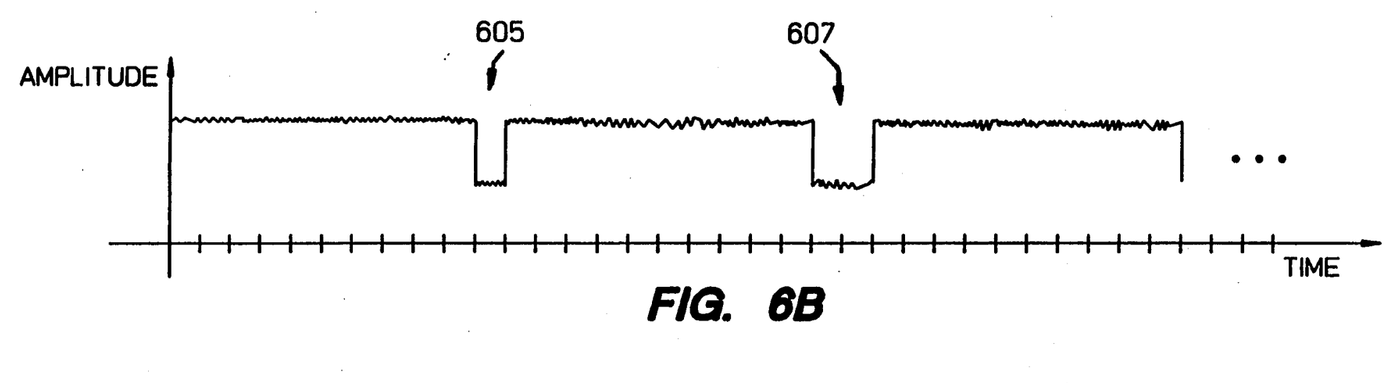
FIG. 6B is a timing diagram representing dark signal samples corresponding to FIG. 6A.

One way of computing the fixed compensation value is to initially vary the time durations of light flow interruption during system start up, as illustrated in a timing diagram shown in FIG. 6A. During system start up, the processor controls the means for interrupting the flow of light to the photoelectric conversion device so as to vary the durations of interruption. For example, the timing diagram of FIG. 6A illustrates a first interruption corresponding to a first well 601 of the timing diagram, and a second interruption corresponding to a second well 603 of the timing diagram. As shown in FIG. 6A, a time duration of the second interruption is twice that of the first interruption. While the flow of light to the photoelectric conversion device is interrupted, the photoelectric conversion device generates the dark signal alone, which comprises dark signal samples, as illustrated in a timing diagram of FIG. 6B. Accordingly, FIG. 6B illustrates a first dark signal sample corresponding to a first well 605 shown in FIG. 6B and a second dark signal sample corresponding to a second well 607 shown in FIG. 6B. As shown in FIG. 6B, the second dark signal sample has a time duration that is twice that of the first dark signal sample. The analog to digital converter digitizes the first and second dark signal samples to respectively produce first and second dark signal values, which are each received by the digital processor. The first dark signal value is doubled and subtracted from the second dark signal value to produce the fixed compensation value.

As discussed herein, the present invention provides an efficient method and apparatus for performing dark signal correction of the desired signal produced by the photoelectric conversion device while substantially preserving fidelity of the desired signal. By filtering the dark signal and subtracting the filtered dark signal from the intermixed signal, the present invention produces the corrected signal, which represents the desired signal at the preferred level of sensitivity and accuracy. As discussed, the contributions are especially valuable in Raman spectroscopy of the surgical patient's air way gasses, wherein light produced by the Raman effect and detected by the photoelectric conversion device is already extremely weak.

Although specific embodiments of the invention have been described and illustrated, the invention is not to be limited to the specific forms or arrangements of parts so described and illustrated, and various modifications and changes can be made without departing from the scope and spirit of the invention. Within the scope of the appended claims, therefore, the invention may be practiced otherwise than as specifically described and illustrated.

What is claimed is:

1. A signal correction method comprising:
   providing a flow of light to a photoelectric conversion device;
   alternately conducting and interrupting the flow of light to the device;
   generating an intermixed signal by means of the device while conducting the flow of light to the device, the intermixed signal including a desired signal intermixed with an unwanted dark signal, the desired signal being generated by the device in response to conducting the flow of light to the device;
   generating a dark signal alone by means of the device while interrupting flow of the flow of light to the device;
   filtering the dark signal alone to produce a filtered dark signal; and
   subtracting the filtered dark signal from the intermixed signal to produce a corrected signal, which is representative of the desired signal.

2. A method as in claim 1 wherein the step of alternately conducting and interrupting the flow of light includes interrupting the flow of light at regular time durations so that the dark signal alone comprises regular dark signal samples.

3. A method as in claim 1 wherein:
   the dark signal alone comprises dark signal samples; and
   the step of filtering the dark signal includes a method for digitally filtering the dark signal samples.

4. A method as in claim 3 wherein the filtering step is performed according to an infinite impulse response digital filtering method.

5. A method as in claim 3 wherein the filtering step is performed according to a finite impulse response distal filtering method.

6. A method as in claim 1 wherein the step of alternately conducting and interrupting the flow of light to the device includes controlling the flow of light to the device so that time periods of light conduction are substantially longer than time periods of light interruption, thereby augmenting an amount of light available to the device for generating the intermixed signal.

7. An apparatus for sensing a flow of light from a light source comprising:
   a means for alternately conducting and interrupting the flow of light from the light source;
   a photoelectric conversion device optically coupled to the light source for generating an intermixed signal while the flow of light is conducted to the device, the intermixed signal including a desired signal intermixed with an unwanted dark signal, the desired signal being generated by the device in response to the flow of light, the photoelectric conversion device generating a dark signal alone while the flow of light from the light source is interrupted;
   a filtering means coupled to the photoelectric conversion device for filtering the dark signal alone to produce a filtered dark signal; and
   a subtraction means coupled to the filtering means and the photoelectric conversion device for subtracting the filtered dark signal from the intermixed signal to produce a corrected signal, which is representative of the desired signal.

8. An apparatus as in claim 7 wherein the means for alternately conducting and interrupting the flow of light interrupts the flow of light during regular time durations so that the dark signal alone comprises regular dark signal samples.

9. An apparatus as in claim 8 wherein the filtering means includes:
   an analog to digital converter coupled to the photoelectric conversion device for generating a set of dark signal sample values in response to the dark signal alone; and
   a digital processor coupled to the analog to digital converter for receiving the set of dark signal sample values and for digitally faltering the values.

10. An apparatus as in claim 9 wherein the digital processor is programmed to digitally filter the sample values according to a finite impulse response digital filtering method.

11. An apparatus as in claim 9 wherein the digital processor is programmed to digitally filter the sample values according to an infinite impulse response digital filtering method.

12. A spectrographic method for analyzing a sample material comprising:

provonding a photoelectric conversion device;

stimulating the sample material to generate a flow of light therefrom;

alternately conducting and interrupting the flow of light from the sample material to the device;

generating an intermixed signal by means of the photoelectric conversion device while conducting the flow of light to the device, the intermixed signal including a desired signal intermixed with an unwanted dark signal, the desired signal being generated by the device in response to conducting the flow of light to the device;

generating a dark signal alone by means of the device during interruptions of the flow of light to the device;

filtering the dark signal alone to produce a filtered dark signal; and subtracting the filtered dark signal from the intermixed signal to produce a corrected signal, which is representative of the desired signal.

13. A spectrographic method as in claim 12 further comprising steps of generating a corrected spectrogram from the corrected signal and displaying the corrected spectrogram on a display device.

14. A spectrographic method as in claim 12 wherein the step of stimulating the sample material includes stimulating the sample material to produce the flow of light by a Raman scattering effect.

* * * * *